US010932650B2

(12) United States Patent
Hale (10) Patent No.: US 10,932,650 B2
(45) Date of Patent: Mar. 2, 2021

(54) MEDICAL SCOPE BUTTON SYSTEM PROVIDING USER FEEDBACK WITHOUT THE NEED FOR DIRECT SIGHT OR ACTIVATION TEST

(71) Applicant: KARL STORZ Imaging, Inc., Goleta, CA (US)

(72) Inventor: Eric Hale, Vancouver, WA (US)

(73) Assignee: KARL STORZ Imaging, Inc., Goleta, CA (US)

( * ) Notice: Subject to any disclaimer, the term of this patent is extended or adjusted under 35 U.S.C. 154(b) by 547 days.

(21) Appl. No.: 15/823,218

(22) Filed: Nov. 27, 2017

(65) Prior Publication Data

US 2019/0159656 A1   May 30, 2019

(51) Int. Cl.
*A61B 1/00* (2006.01)
*A61B 1/005* (2006.01)
*A61B 1/05* (2006.01)
*G06F 3/0354* (2013.01)
*G06F 3/038* (2013.01)

(52) U.S. Cl.
CPC ...... *A61B 1/00039* (2013.01); *A61B 1/00006* (2013.01); *A61B 1/0016* (2013.01); *A61B 1/00045* (2013.01); *A61B 1/0052* (2013.01); *A61B 1/00055* (2013.01); *A61B 1/00066* (2013.01); *A61B 1/00133* (2013.01); *A61B 1/05* (2013.01); *G06F 3/038* (2013.01); *G06F 3/03545* (2013.01); *G09G 2380/08* (2013.01)

(58) Field of Classification Search
CPC ...... A61B 1/00039; A61B 1/043; A61B 1/045
USPC .................................................. 600/131, 118
See application file for complete search history.

(56) References Cited

U.S. PATENT DOCUMENTS

| 9,113,880 B2 | 8/2015 | Zemlok | |
|---|---|---|---|
| 2007/0049798 A1* | 3/2007 | Urasaki | A61B 1/00011 600/118 |
| 2008/0097151 A1 | 4/2008 | Inoue | |
| 2014/0267812 A1 | 9/2014 | Kennedy | |
| 2016/0367114 A1* | 12/2016 | Iizuka | G02B 23/24 |

FOREIGN PATENT DOCUMENTS

| JP | 2012-124627 A | 6/2012 |
|---|---|---|
| JP | 2012124627 A * | 6/2012 |

OTHER PUBLICATIONS

Doyle, A. European Search Report; App 18208516.7-1124, dated Apr. 10, 2019, pp. 1-9, Munich.

* cited by examiner

*Primary Examiner* — Alexandra L Newton
*Assistant Examiner* — Rynae Boler
(74) *Attorney, Agent, or Firm* — Michael Loi; David Villalpando (57) ABSTRACT

Systems and methods are provided for improved control feedback of medical scopes. Buttons on a scope include both touch sensors and button press sensors. The touch sensors activate independently of a button press when a mere touch is applied to the button, causing a function indication to be displayed, preferably on the scope video display, showing which function will activate if the button is pressed. Touch indications may also be displayed identifying the button that is pressed. The buttons may be reconfigured along with the function and touch indications. Such a feedback scheme allows improved operation and safety as the operator does not need to look away from the display to identify a button to be pressed.

17 Claims, 5 Drawing Sheets

MEDICAL SCOPE BUTTON SYSTEM PROVIDING USER FEEDBACK WITHOUT THE NEED FOR DIRECT SIGHT OR ACTIVATION TEST

TECHNICAL FIELD OF THE INVENTION

The invention relates generally to the field of medical imaging scopes and more specifically to endoscope designs for improving user control of medical scopes.

BACKGROUND OF THE INVENTION

Figure 1:
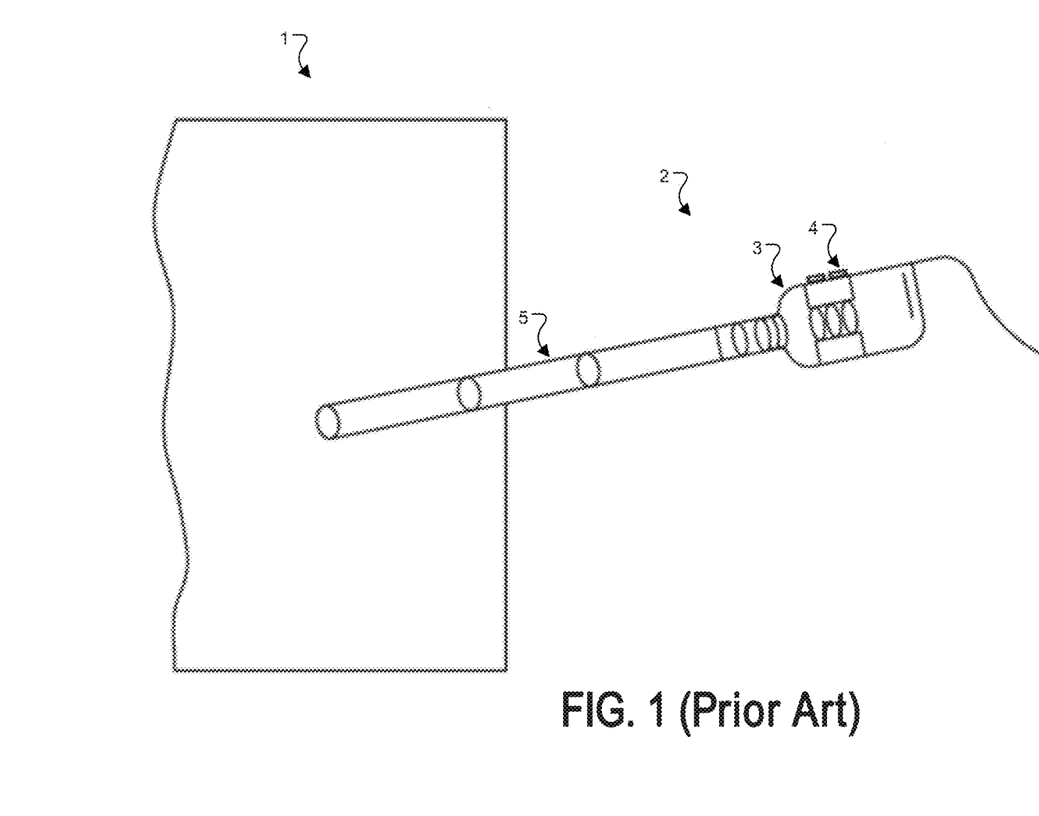
FIG. 1 is diagram of a prior art endoscopic system.

A typical prior art endoscope 2, as illustrated in FIG. 1, usually includes a first imaging lens (e.g., an objective) followed by a series of carrier lenses (e.g., relays) in the scope shaft 5 which capture and transmit an optical image from inside an enclosed area 1 to the outside. The proximal end of the endoscope 2 may be attached, via direct coupling or an adaptor, to a camera head 3 or an eye-piece for viewing. The camera head 3 usually includes lenses for receiving the optical image and forming a real optical image onto the image sensor. The digital image captured by the image sensor can then be transmitted to a camera control unit (CCU) or other similar modules for analysis and display. Typically, two or more buttons 4 are positioned on an outer surface of the camera head 3, usually the top surface, but buttons may be positioned on multiple surfaces.

Some endoscope systems have a number of buttons, which can be reconfigured to change their function, for example when the endoscope is used in a different mode or when more complex functions are desired to be controlled easily by the buttons versus other user input which require either the operator moving their hand from the procedure to the system user inputs, or another operator to follow commands from a lead operator.

When the buttons are reconfigured, the button function should be tested or confirmed before use in the procedure. However some functions, such as fluorescent imaging light emission or any surgical attachments, are not desired to be activated simply to test that the proper configuration is applied. Further, the testing or confirmation process can slow down the procedure; with deleterious effects on overall efficiency the more often button functions are tested.

Finally, often there are few buttons, such as two or three, present on an endoscope to reduce the complexity and likelihood of an accidental button press. The button position is provided outside of the region where an operator grips the handle or camera head, but within easy finger or thumb reach of the grip, such as under the range of movement of the thumb. An operator frequently needs to use one hand to position the scope and another to operate a surgical instrument or operate a diagnostic process such as metrology for industrial applications. The button positioning may make it difficult for the operator to "feel" or confirm with tactile feedback that a finger or thumb is on one of the buttons desired to be pressed, resulting in the need for the operator to look from the screen to the endoscope device to confirm the button location, especially when shifting grip on the endoscope device or changing between buttons. Surgical hoods or other items may also block the operator's direct view of the endoscope device handle. It would be better for the operator to be able to confirm the proper button is about to be pressed without looking at the device to enable continuous viewing of the display.

What is needed are systems and methods to enable better control of an endoscopic camera in operating conditions where the surgeon or other operator at times needs to pay careful or uninterrupted attention to the scope display. What are also needed are systems and methods to improve operating speed and safety when using medical scopes.

SUMMARY OF THE INVENTION

It is an object of the invention to improve the operation of a medical scope such as an endoscope with feedback to the operator. It is a further object of the invention to improve the testing of button reconfigurations on a medical scope. It is also a further object of the invention to enable an operator to identify buttons to be pressed on a scope without looking away from the scope video display.

In order to achieve these objects, various aspects of the invention provide systems and methods are provided for improved control feedback of medical scopes. A program product for operation on a camera control module or other control system of scope a scope including both touch sensors and button press sensors on the buttons is also provided. Buttons on a scope include both touch sensors and button press sensors. The touch sensors activate independently of a button press when a mere touch is applied to the button, causing a function indication to be displayed, preferably on the scope video display, showing which function will activate if the button is pressed. Touch indications may also be displayed identifying the button that is pressed. The buttons may be reconfigured along with the function and touch indications. Such a feedback scheme allows improved operation and safety as the operator does not need to look away from the display to identify a button to be pressed.

According to a first aspect of the invention, a medical scope system is provided including a medical scope including a scope shaft, a handle attached to the scope shaft having a plurality of control buttons disposed along at least one surface of the handle, two or more of the control buttons including a depression activation circuit operable to create a depression activation signal when pressed, and a touch detection circuit operable to create a touch detection signal when touched, independently of being pressed. The system includes a camera control module including an electronic controller communicatively coupled to the medical scope and operable to receive the depression activation signals and the touch detection signals from the two or more control buttons. A display device is communicatively coupled to the camera control module. The camera control module electronic controller is programmed to, in response to receiving a touch detection signal from a respective button of the two or more control buttons, display a function indication on the display device indicating that the respective button is presently being touched and identifying a function that the respective button is configured to activate when the button is pressed in a present mode of operation.

According to some implementations of the first aspect, the camera control module electronic controller is programmed to display a touch indication communicating that the touched button is presently being touched and identifying the touched button.

According to some implementations of the first aspect, the buttons may be provided with different modes, and the camera control module electronic controller is programmed to detect that the touched button is pressed through the depression activation signal, and in response activate the function that the touched button is configured to activate in a present mode of operation. The camera control module may operable to reconfigure the scope into at least two modes of operation in which at least one button function differs between the at least two modes.

According to some implementations of the first aspect, displaying the function indication further includes displaying a list of two or more functions and displaying the touch indication includes highlighting or otherwise visually emphasizing on the display the function associated with the respective touched button. Displaying the list of two or more functions may include displaying the functions presented in the order of the physical order on the scope device of their associated two or more buttons.

According to some implementations of the first aspect, the camera control module electronic controller is further programmed to, in response to receiving a touch removal signal or in response to a discontinuation of the touch detection signal, remove the displayed function notification.

According to some implementations of the first aspect, the medical scope is further operable to detect a second operator touch of a different, second button on the medical scope and, in response to detecting the second operator touch, transmit a second touch detection signal to a camera control module identifying a second touched button. The camera control module receives the second touch detection signal and in response, causes the electronic display to display a second function notification indicating that the second touched button is presently being touched and identifying a different, second function that the second touched button is presently configured to activate if pressed or mechanically displaced.

According to a second aspect of the invention, a method is provided for operating a medical scope system. The method includes detecting an operator touch of a button on a medical scope, the button capable of both touch detection and pressure or mechanical displacement activation. In response to detecting the operator touch, the method transmits a touch detection signal to a camera control module identifying a touched button among a group of multiple buttons. The touch detection signal is received at the camera control module which, in response, causing an electronic display to display a function indication identifying a function that the touched button is presently configured to activate if the button is pressed or mechanically displaced.

According to some implementations of the second aspect, the method includes displaying a touch indication communicating that the touched button is presently being touched and identifying the touched button. Displaying the function indication may further include displaying a list of two or more functions and displaying the touch indication includes highlighting or otherwise visually emphasizing on the display the function associated with the touched button. Further, displaying the list of two or more functions may include displaying the functions presented in the order of the physical order on the scope device of their associated two or more buttons.

According to some implementations of the second aspect, the method detects that the touched button is pressed, and in response activates the function that the touched button is configured to activate in a present mode of operation.

According to some implementations of the second aspect, the method includes receiving a medical scope mode change control input, and in response changing the function of at least one of the group of buttons will activate if pressed or mechanically displaced.

According to some implementations of the second aspect, the method includes detecting a simultaneous operator touch of two or more buttons in the group of multiple buttons, and in response causing the electronic display to display a multiple function indications communicating that the two or more buttons are touched simultaneously and communicating the functions of each touched button or a different function to be activated if both button are pressed simultaneously.

According to some implementations of the second aspect, the method includes detecting a touch removal from the touched button and, in response, removing the function indication. The method may also include detecting a second operator touch of a different, second button on the medical scope and, in response to detecting the second operator touch, transmitting a second touch detection signal to a camera control module identifying a second touched button among the group of multiple buttons. The second touch detection signal is received at the camera control module which, in response, causing an electronic display to display a function indication identifying a different, second function that the second touched button is presently configured to activate if pressed or mechanically displaced.

According to a third aspect of the invention, a program product is provided stored on one or more tangible, non-transitory computer readable media and executable by at least one electronic controller on a scope device and/or a camera control module to perform the various method steps according to the second aspect.

These and other features of the invention will be apparent from the following description of the preferred embodiments, considered along with the accompanying drawings.

BRIEF DESCRIPTION OF THE DRAWINGS

The present invention will become more fully understood from the detailed description given herein and the accompanying drawings which are given by way of illustration only, and thus are not limitative of the present invention, and wherein.

DETAILED DESCRIPTION OF EXAMPLE EMBODIMENTS

As used herein, first elements (e.g., sensors and lenses) that are "optically arranged" in relation to other elements, refers to the first elements' position along a common optical path that includes first and other elements. For example, a lens group optically arranged between an image sensor and an objective, means that the lens group occupies a portion of the optical path that light travels (e.g., from the objective to the image sensor) for capturing images or video.

Because digital cameras and FI sensors and related circuitry for signal capture and processing are well-known, the present description will be directed in particular to elements forming part of, or cooperating more directly with, a method and apparatus in accordance with the invention. Elements not specifically shown or described herein are selected from those known in the art. Certain aspects of the embodiments to be described are provided in software. Given the system as shown and described according to the invention in the following materials, software not specifically shown, described or suggested herein that is useful for implementation of the invention is conventional and within the ordinary skill in such arts.

Figure 2:
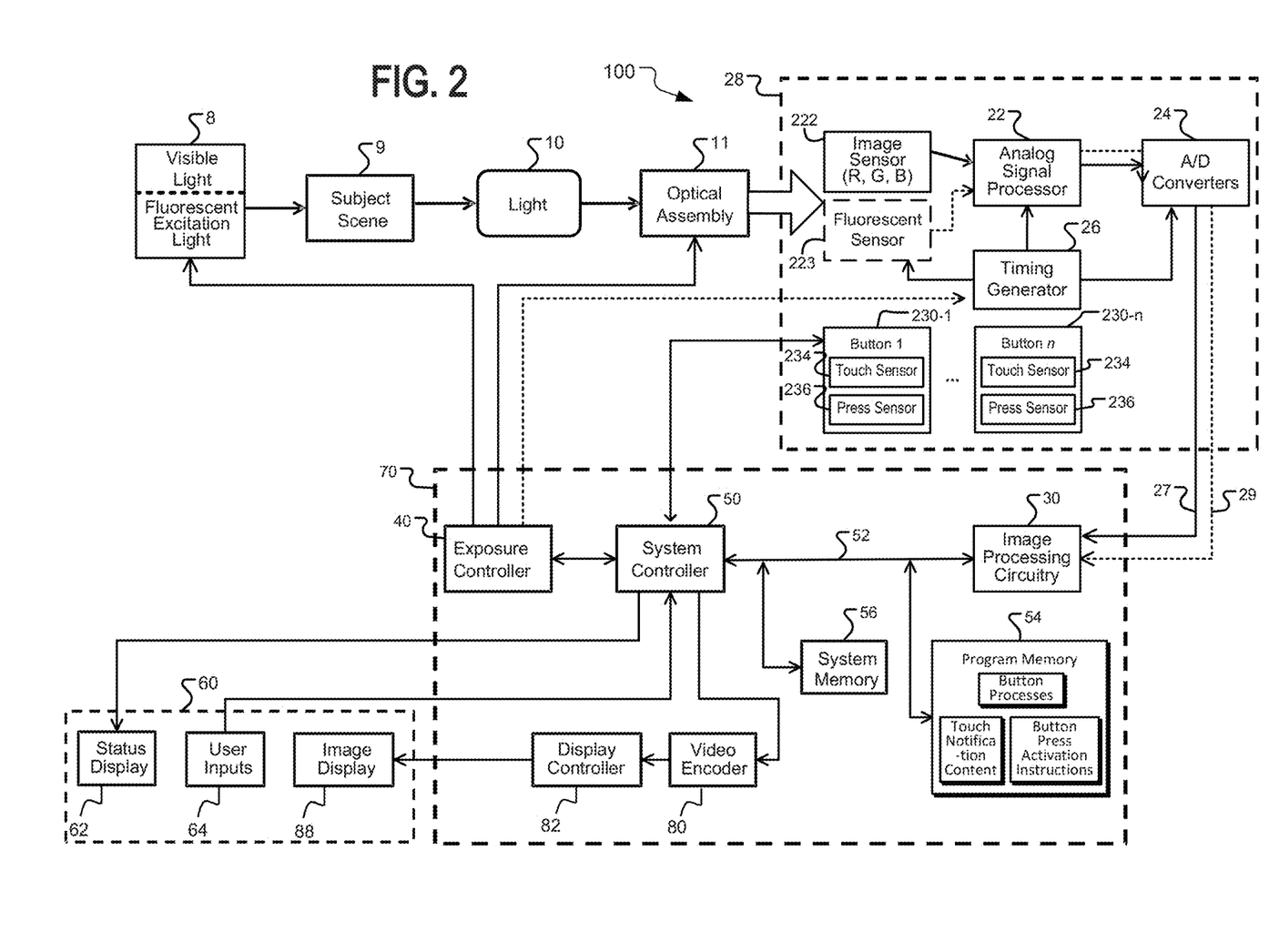
FIG. 2 is a hardware block diagram of an example system including medical scope, a camera control module, and an electronic display.

Referring to FIG. 2, shown is a system hardware block diagram of an example system including a medical scope 100, a camera control module 70, and a user interface 60 including one or more displays, the system being one example hardware design on which the improved button control and feedback techniques described herein may be implemented. The medical scope 100 in this system is a dual mode visible light and fluorescence imaging (FI) endoscope. However, this is not limiting and features and techniques herein may be employed with many types of scopes, including visible light only scopes. Of the depicted blocks, scope 100 includes the optical assembly 11 and the camera head and handle 28 ("camera head", "handle") which may be detachable from the scope shaft or may be integrated with the shaft as in the prior art scope of FIG. 1. The scope also includes the light source 8. The invention is applicable to more than one type of device enabled for image capture, such as endoscopes, other medical imaging devices, and digital microscopes, for example. The preferred version is an imaging scope system, such as an endoscope.

In this embodiment, the camera head 28 includes two or more buttons 230, labeled button 230-1 through button 230-n to illustrate there may be more. In some examples, button 230-n may be referred to as a second button 230-2. The buttons 230 may be located at any desired surface of the handle 28 or other assemblies attached thereto. Two or more of the buttons are improved with both a touch sensor 234 and button press sensor 236, such as a typical mechanical button switch or pressure sensor. The touch sensors 234 are preferably projected capacitive touch sensors, but may be any suitable type of touch sensor such as infrared touch sensors, surface acoustic wave touch sensors, or resistive touch sensors. For medical applications the touch sensors 234 should be capable of detecting user finger or thumb touches even through a latex or hypoallergenic surgical glove. Other applications such as equipment repair endoscopes, for example, may also require ability to sense finger or thumb touches through a glove.

The touch sensor selected should not require significant pressure to activate it as compared to the button press sensor, because the user feedback systems herein employ the touch sensor to detect when the button is touched but not pressed. For example, pressure required to activate the touch sensor (if the touch sensor type requires pressure at all), should be less than 50% of that required to activate the button press sensor, and preferably less than 10%. In the best case, a technology such as projected capacitive touch sensors are used which do not inherently require any pressure to activate. The type of button press sensor employed may be any suitable button switch that can be used in the desired environment, such as an operating room for medical endoscopes. The button press sensors 236 are typically electrical switches activating features or mechanisms by electrical control, but this is not limiting and mechanical button actuation could possibly be used in some versions. Further, the different buttons 1-n may have different types of the button press sensors 238, depending on their size, position, and function. Momentary (non-latching) buttons or toggle buttons may be used. In prior systems, typically if touch sensors are used in a system with buttons, they are used to replace the button press sensor such that a user touch activates the button, or for another type of sensor input such as a touchpad or touch strip. However, in the systems herein, the touch sensors 234 are presented along the top contact surface of the respective button 230, but act independently of the button sensor to provide user feedback to improve system operation. The user feedback scheme will be further described with respect to later drawings.

Buttons 230 may have power supply, biasing circuitry, and control circuitry mounted in the handle 28, which may be on a circuit board on which the buttons 230 are mounted, or may be integrated with the analog signal processor or another controller chip present in the handle. Alternatively, buttons 230 may be connected by a dedicated sensor bus or dedicated signal paths to analog signal processor 22, or system controller 50 in the camera control module 70, or another controller within the camera head 28. The remainder of the depicted system will now be described in order to better understand the operation of the improved user feedback provided by the techniques herein.

As shown, a light source 8 illuminates subject scene 9 with visible light and/or fluorescent excitation light. Light source 8 may include a single light emitting element configured to provide light throughout the desired spectrum, or a visible light emitting element and a one or more fluorescent excitation light emitting elements. Further, light source 8 may include fiber optics passing through the body of the scope, or other light emitting arrangements such as LEDs or laser diodes positioned at or near the front of the scope. As shown in the drawing, light 10 reflected from the subject scene (or fluorescent light emitted from the subject scene) is passed to an optical assembly 11, where the light is focused toward an image sensor assembly to form an image at a solid-state image sensor(s) 222 and/or a fluoresced light sensor 223. The fluorescent light elements are shown in dotted lines as optional, because visible light only scopes may be used. While visible light scopes are used more than fluorescence imaging (FI) scopes, the FI scopes have more button functions needed to accomplish changing between visible and FI mode, and thus can benefit greatly from the techniques described herein.

Optical assembly 11 includes at least one lens, which may be a wide-angle lens element such that optical assembly 11 focuses light which represents a wide field of view. Portions of the optical assembly may be embodied in a camera head 28, while other portions are in an endoscope shaft. In some embodiments of the invention, the scope handle 28 contains control electronics but the image sensor(s) is located in the scope shaft itself, often toward the distal end of the shaft. The optical assembly 11 may be contained in a single imaging device with the image sensor assembly. Image sensor 222 (which may include separate R, G, and B sensor arrays or a single array with color sensitive individual pixels) and fluoresced light sensor 223 convert the incident visible and invisible light to an electrical signal by integrating charge for each picture element (pixel). The image sensor 222 and fluoresced light sensor 223 may be active pixel complementary metal oxide semiconductor sensor (CMOS APS) or a charge-coupled device (CCD), or other suitable image sensor.

Timing generator 26 produces various clocking signals to select rows and pixels and synchronizes the operation of image sensor 222 and fluorescent sensor 223, analog signal processor 22, and A/D converter 24. The image sensor assembly typically includes the image sensor 222 and fluorescent sensor 223, adjustment control 20, the analog signal processor 22, the A/D converter 24, and the timing generator 26. The functional elements of the image sensor assembly can be fabricated as a single integrated circuit as is commonly done with CMOS image sensors or they can be separately-fabricated integrated circuits.

The total amount of light 10 reaching the image sensor 222 and/or fluoresced light sensor 223 is regulated by the light source 8 intensity, the optical assembly 11 aperture, and the time for which the image sensor 222 and fluoresced light sensor 223 integrates charge. An exposure controller 40 responds to the amount of light available in the scene given the intensity and spatial distribution of digitized signals corresponding to the intensity and spatial distribution of the light focused on image sensor 222 and fluoresced light sensor 223. Exposure controller 40 also controls the emission of fluorescent excitation light from light source 8, and may control the visible and fluorescent light emitting elements to be on at the same time, or to alternate them to allow fluoresced light frames to be captured in the absence of visible light if such is required by the fluorescent imaging scheme employed. Exposure controller 40 may also control the optical assembly 11 aperture, and indirectly, the time for which the image sensor 222 and fluoresced light sensor 223 integrate charge. The control connection from exposure controller 40 to timing generator 26 is shown as a dotted line because the control is typically indirect.

Analog signals from the image sensor 222 and fluoresced light sensor 223 are processed by analog signal processor 22 and applied to analog-to-digital (A/D) converter 24 for digitizing the analog sensor signals. The digitized signals each representing streams of images or image representations based on the data, are fed to image processor 30 as image signal 27, and first fluorescent light signal 29. For versions in which the image sensor 222 also functions to detect the fluoresced light, fluoresced light data is included in the image signal 27, typically in one or more of the three color channels.

Image processing circuitry 30 includes circuitry performing digital image processing functions to process and filter the received images as is known in the art. Image processing circuitry may include separate, parallel pipelines for processing the visible light image data and the FI image data separately. Such circuitry is known in the art and will not be further described here. Image processing circuitry 30 may provide algorithms, known in the art, for combining visible light imagery with FI imagery in a combined image display, and further highlighting emphasizing the FI imagery for easily distinguishing the presence of fluorescing features in the image.

The system controller 50 controls the overall operation of the image capture device based on a software program stored in program memory 54. This memory can also be used to store user setting selections and other data to be preserved when the camera is turned off.

System controller 50 controls the sequence of data capture by directing exposure controller 40 to set the light source 8 intensity, the optical assembly 11 aperture, and controlling various filters in optical assembly 11 and timing that may be necessary to obtain image streams based on the visible light and fluoresced light. In some versions, optical assembly 11 includes an optical filter configured to attenuate excitation light and transmit the fluoresced light. A data bus 52 includes a pathway for address, data, and control signals.

Processed image data are continuously sent to video encoder 80 to produce a video signal. This signal is processed by display controller 82 and presented on image display 88. This display is typically a liquid crystal display backlit with light-emitting diodes (LED LCD), although other types of displays are used as well. The processed image data can also be stored in system memory 56 or other internal or external memory device.

The user interface 60, including all or any combination of image display 88, user inputs 64, and status display 62, is controlled by a combination of software programs executed on system controller 50, receiving input from user inputs 64 and from buttons 230. User inputs 64 typically include some combination of typing keyboards, computer pointing devices, buttons, rocker switches, joysticks, rotary dials, or touch screens. The system controller 50 manages the graphical user interface (GUI) presented on one or more of the displays (e.g. on image display 88). In particular, the system controller 50 will typically have a mode toggle user input (typically through a configurable button 230 or on the endoscope or camera head itself, but possibly through a GUI interface), and in response transmit commands to adjust image processing circuitry 30 based on predetermined setting stored in system memory. Preferably a system employed with any of the device designs herein provides ability to toggle between at least two modes, visible light and FI modes.

Image processing circuitry 30 is one of three programmable logic devices, processors, or controllers in this embodiment, in addition to a system controller 50 and the exposure controller 40. Image processing circuitry 30, controller 50, exposure controller 40, system and program memories 56 and 54; video encoder 80 and display controller 82 may be housed within camera control module (CCM) 70.

CCM 70 may be responsible for powering and controlling light source 8, the image sensor assembly, and/or optical assembly 11, and may power and receive signals directly from the buttons 230, or indirectly if buttons 230 pass their signals through a controller in the camera head such as the analog signal processor. Such power and control connections are not depicted separately but will typically be contained in a single flexible cable with data connections 27 and 29. In some versions, a separate front end camera module may be connected between camera head 28 and CCM 20 to perform some of the image processing functions of image processing circuitry 30.

Although this distribution of imaging device functional control among multiple programmable logic devices, processors, and controllers is typical, these programmable logic devices, processors, or controllers can be combinable in various ways without affecting the functional operation of the imaging device and the application of the invention. These programmable logic devices, processors, or controllers can comprise one or more programmable logic devices, digital signal processor devices, microcontrollers, or other digital logic circuits. Although a combination of such programmable logic devices, processors, or controllers has been described, it should be apparent that one programmable logic device, digital signal processor, microcontroller, or other digital logic circuit can be designated to perform all of the needed functions. All of these variations can perform the same function and fall within the scope of this invention.

Figure 3:
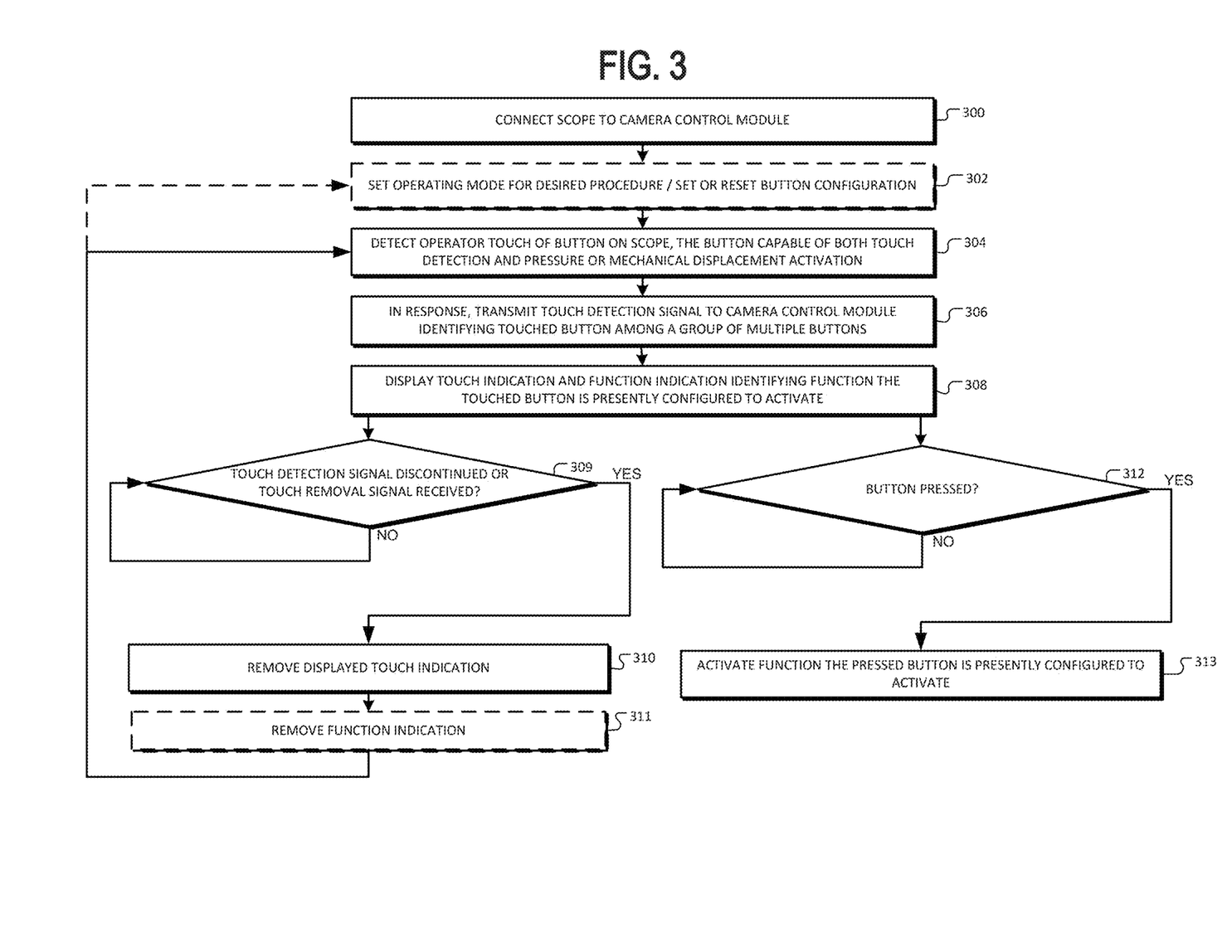
FIG. 3 is a flowchart of an example feedback control process.

FIG. 3 is a flowchart of a user feedback process according to an example embodiment. The process may be conducted on a device like that of FIG. 2, or another medical scope device and system including buttons for which the system can detect and differentiate touches and button presses. Generally the process is conducted by system controller 50 executing program code stored in tangible non-transitory program memory 54 (FIG. 2). In some cases, programming in the scope device analog signal processor 22 or another onboard processor may perform the function of interpreting sensor signals from buttons 230. The process begins at block 300 where the scope is connected to the camera control module (CCM) or other suitable control system. Some scopes may have an integrated camera control module and may connect directly to the display/user input system, or connect to a CCM over a network. After the scope is connected and powered on, the process at block 302 includes setting the operating mode of the scope for the desired procedure. Some scopes may have multiple button configurations, which change the function of buttons 230. Block 302 also includes setting or resetting the button configuration to a desired configuration. The button configuration or mode or both may be changed often within a procedure such as a surgery or diagnostic procedure. At this point in the process the scope is ready to begin a medical procedure.

The touch feedback part of the process starts at block 304, where the operator touches a button on the medical scope and the process detects the operator touch of a button on a medical scope, the button capable of both touch detection and pressure or mechanical displacement activation as discussed above. Note that the operator is merely touching, not pressing the button at this point to activate the button. The touch detection allows the operator to test the configuration of the button after a reconfiguration, or to allow the operator to confirm the correct button is pressed while keeping a constant view on the video screen (by the notification at step 308). Such ability presents an important safety and speed advantage, especially with regard to surgical procedures. Next, at block 305, in response to detecting the operator touch, the process transmits a touch detection signal to a camera control module identifying a touched button among a group of multiple buttons. As discussed with respect to the button hardware in FIG. 2, the signal may transmit through a signal wire or sensor bus extending through the scope cable directly to the CCM, or may be received first from the touch sensor by a local controller in the camera head 28 and transmitted to the CCM from there, in an encoded fashion or as a notification signal rather than a raw sensor signal. That is, the interpretation of raw sensor data, including filtering and threshold recognition, and the resulting logical decision that a touch is detected may occur in a controller such as the analog signal processor 22 (FIG. 2), or may occur in the system controller 50. The interpretation of touch sensor signals is known in the art for each type of sensor, and will not be further described here. The design process should, of course, take into account medical gloves where applicable. No matter where the touch sensor signal is interpreted, either a raw or partially processed touch sensor signal, or a notification signal of the results of touch sensor signal interpretation, constitute transmitting a touch detection signal.

The transmitted signal will include a way of identifying the touched button, such as by a touch sensor ID on a digitally polling sensor bus, or separate signal lines for each sensor. If the touch sensor interpretation is done in the analog signal processor 22 or another processor within the camera head 28, an identifier for the touch sensor is sent as part of the touch detection signal. Note that the touch detection signal may be continuously transmitted during a touch, and then removed at the end of the touch, or may be part of a "touch down", "touch up" type signal scheme that is only transmitted when such a change occurs. If sensor data is interpreted at the CCU, the sensor data for each button is sent continuously to the CCU, typically from an A/D converter integrated with the touch sensor over a sensor power/data bus, but analog signals may also be used.

Figure 4:
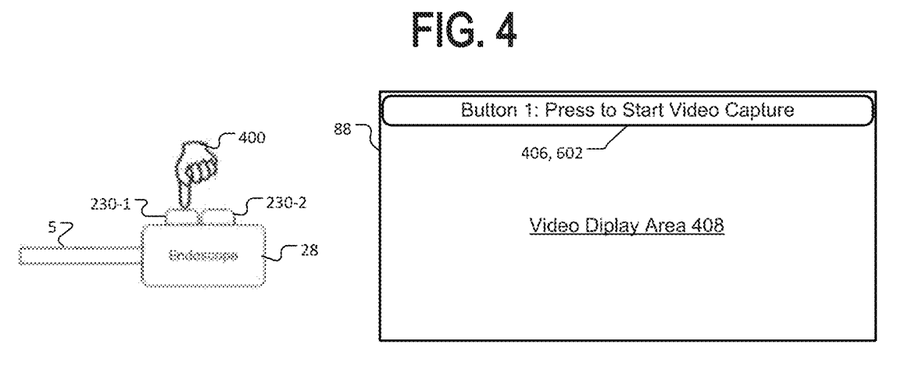
FIGS. 4-5 show a sequence of action diagrams and their resulting feedback display according to an example embodiment.

Next at block 308, the process receives the touch detection signal at the camera control module and in response, causes an electronic display to display a touch indication communicating that the touched button identified is presently being touched, and display a function indication identifying a function that the touched button is presently configured to activate if pressed or mechanically displaced. An example of such a display is shown in FIG. 4, which depicts a stylized diagram showing the operator 400 finger touch of a first button 230-1 of two buttons 230. The resulting touch indication 406 and function indication 602 is shown on the display, which may be the image display 88 or the status display 62 of (FIG. 1). The function indication 602 is the text identifying the function, while the touch indication may include merely the appearance of the function indication, or my also include an explicit identification of the button such as the text "Button 1:" before the function indication. Preferably the video display 88 is used, which simultaneously shows the video display area 408 for the scope video if the video is active at the time, to allow the added advantages of allowing the surgeon to see the touch indication 406 and function indication 602 without looking away from the screen with the scope video. Some embodiments may not separately identify the button, instead identifying the button only indirectly through the function indication 602, such as the example "Press to Start Video." Note that in this version the touch indication identifies the button touched in text "Button 1", which may be any suitable description such as "front button" or "button A", for example.

Figure 5:
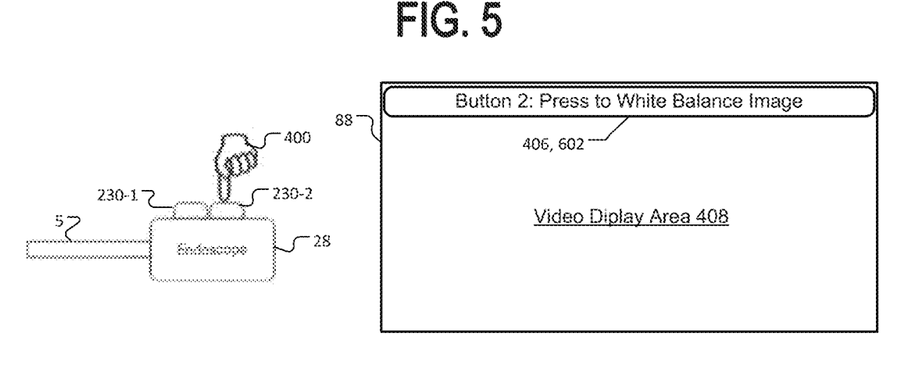

FIG. 5 is a similar diagram depicting what occurs if the operator moves to touch a second button 230-2 of the two buttons 230. Referring again to FIG. 3, the steps to accomplish this are depicted by the loop through blocks 309, 310, and 311, and back to block 304. Note that at any point, the process may be interrupted by the operator pressing the button, resulting in a button press signal received at block 312, which results in the configured function being activated at block 313. Different versions may display different indications regarding such function activation. The touch indication displayed at block 308 may be removed, or may be maintained as long as the operator still touches the button that has been pressed. Preferably, the indication 406 (FIG. 4) is either augmented or replaced to display an activation indication that the function has been activated. Such indication may last as long as the button is held down, for functions which may be held active for a period of time. For a function that takes a discrete amount of time, the activation indication may be displayed momentarily for a predesignated time, such as one second. Referring again to FIG. 3, at block 309 the process detects when the operator stops touching the button, by the touch signal being discontinued or a signal indicating a "touch up" or that a touch is been removed. The signal may vary, as discussed above, depending on where the touch sensor signal is interpreted, and which signaling scheme is desired.

At block 309 of FIG. 3, the process can also respond to a button press claim further comprising detecting that the touched button is pressed, and in response activating the function that the touched button is configured to activate in a present mode of operation. As long as the operator touches the button, the process at block 309 follows the depicted NO branch, returning to block 309 to wait for the touch to be removed. For designs in which a "touch up" signal is used at this point, the process may be interrupt driven, or may be loop driven. The particular programming may vary, but the function remains the same, that is to keep displaying the touch indication until the touch signal is removed.

When the touch signal is removed, or a "touch up" type signal is received, the process goes to block 310, where it removes the display touch indication. In some embodiments, the process also removes the function indication as shown at block 311. For example, in the embodiment shown in FIG. 4 and FIG. 5, the touch indication 406 will be removed entirely when the touch is removed, including the identification of the button touched, and the function indication identifying the function of the touched button. In other embodiments, the touch indication may be separate from the function indication.

Figure 6:
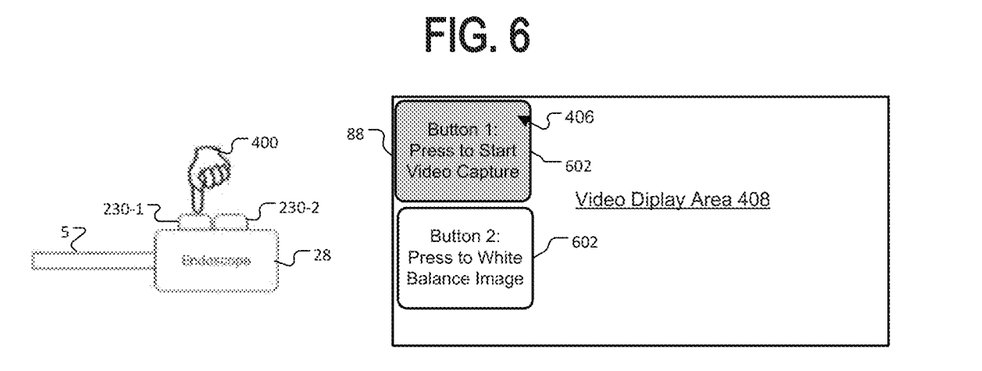
FIGS. 6-7 show a similar sequence of diagrams for another example embodiment.
Figure 7:
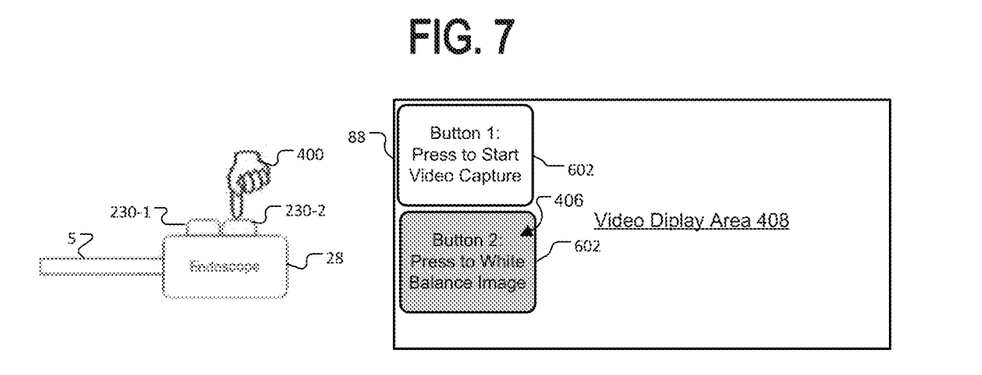

An example of this is shown in the sequence of FIG. 6 and FIG. 7. In these diagrams, the operator touches the front button 1, and then moves to touch the back button 1. When a touch is made, the FIG. 3 process for this embodiment will at block 306 display both of the function indications 602, and display a touch indication as a highlight or other visual emphasis, like a different color like green for the button being touched, and no special color or a gray for the function indication 602 of the button not being touched. In this embodiment, the user is able to see a list of more than one button function, which can provide an advantage for scenarios in which the button function is reconfigured frequently, or there are multiple buttons and the reconfiguration of the buttons may make it difficult for the operator to remember the configuration of all buttons. Note while two button function indications 602 are displayed, this is not limiting and more may be displayed if there are more buttons 230 on the scope device.

Some versions may display a function indication for every button, while some may display a group of function indications 602, such as for all the buttons in a particular physical group on the scope device. For example if there are two buttons 230 on the top of the scope camera head 28, and two buttons on the side (not shown), when a top button is touched, the process may display function indications 602 for both of the top buttons 230, and when a side button is touched the process may display function indications 602 for both of the side buttons. In each case, the button actually touched is identified with a touch indication 406 such as a visual highlight, visual emphasis, or color change as discussed above. In such embodiments, a visual emphasis may include enlarging the function indication 602 relative to the other function indications displayed. The displayed group of function indications 602 may be considered as a list of two or more functions. Displaying such a list may include displaying the functions presented in the order of the physical order on the scope device of their associated two or more buttons. That is, the top first button 230-1 and the top second button 230-2 will typically be listed in physical order.

When the operator touch is removed for example from first button 230-1 as shown in FIG. 6, the process of FIG. 3 at block 310 removes the displayed touch indication 406, returning both function indication 602 to the same non-highlighted display state, but does not remove the function indications at block 311, shown by the dotted lines indicating that block 311 is optional. Then, as shown in FIG. 7, when the operator touches the second button 230-1, the button indication 406 is added to the function indication 602 for button 2. Especially in embodiments such as this one that display function indications, a separate identification of the button touched, for example the text saying "Button 1" and "Button 2" may not be displayed. In such case, the touch indication 406 consists of the highlight or visual emphasis added to the display for the function indication 602.

Referring again to FIG. 3, as depicted the process may return to block 302, whenever the operator through the user interface reconfigures the scope device mode or reconfigures the buttons. In such case, the process loads the function indications (preferably stored in program memory 54, FIG. 2) into active memory for display of the function indications 602, where the combined touch indications and function indications of FIG. 4 and FIG. 5. This reconfiguration process also, of course, loads the respective function controls for activating the functions from program memory. Thus, the process at block 302 includes receiving a medical scope mode change control input, and in response changing the function of at least one of the group of buttons that will activate if pressed or mechanically displaced.

While the process is depicted as a flowchart including loops, the actual program code implementing the process is typically interrupt driven and changes between multiple states when receiving user inputs from the user interface and buttons. As such, the function activation shown at block 313 occurs while the touch indication from block 308 is displayed. In some versions, a short delay such as 500 milliseconds may be provided between blocks 306 and 308, such that if an operator moves directly to press the button then removes their finger or thumb from the button without resting their finger or thumb on it in a touch position, the display will not flash a touch indication momentarily.

The process may further include detecting a simultaneous operator touch of two or more buttons in the group of multiple buttons, and in response causing the electronic display to display a multiple touch indication communicating that the two or more buttons are touched simultaneously. A warning may also be displayed in this case. Depending on the desired configuration, multiple simultaneous button presses may be allowed, or may not be allowed. The response to such scenarios depends on the particular functions being executed, and is known in the art so will not be further discussed here. In some cases, pressing two buttons simultaneously may activate a different function than merely the combination of both individual button functions. In this case, such a touch will result in the dual button function being displayed as the function indication, and the touch indication will be displayed for both buttons, identifying both touched buttons for two buttons that are touched but not pressed, if a separate touch indication such as the text identifying the pressed button in touch indication 406 of FIGS. 4-5, or the highlighted touch indication 406 applied to the function indication 602 in FIGS. 6-7.

As used herein the terms "comprising," "including," "carrying," "having" "containing," "involving," and the like are to be understood to be open-ended, that is, to mean including but not limited to. Any use of ordinal terms such as "first," "second," "third," etc., in the claims to modify a claim element does not by itself connote any priority, precedence, or order of one claim element over another, or the temporal order in which acts of a method are performed. Rather, unless specifically stated otherwise, such ordinal terms are used merely as labels to distinguish one claim element having a certain name from another element having a same name (but for use of the ordinal term).

The foregoing has outlined rather broadly the features and technical advantages of the invention in order that the detailed description of the invention that follows may be better understood. It should be appreciated by those skilled in the art that the conception and specific embodiments disclosed may be readily utilized as a basis for modifying or designing other structures for carrying out the same purposes of the invention. It should also be realized by those skilled in the art that such equivalent constructions do not depart from the scope of the invention as set forth in the appended claims.

Although the invention and its advantages have been described in detail, it should be understood that various changes, substitutions and alterations can be made herein without departing from the scope of the invention as defined by the appended claims. The combinations of features described herein should not be interpreted to be limiting, and the features herein may be used in any working combination or sub-combination according to the invention. This description should therefore be interpreted as providing written support, under U.S. patent law and any relevant foreign patent laws, for any working combination or some sub-combination of the features herein.

Moreover, the scope of the present application is not intended to be limited to the particular embodiments of the process, machine, manufacture, composition of matter, means, methods and steps described in the specification. As one of ordinary skill in the art will readily appreciate from the disclosure of the invention, processes, machines, manufacture, compositions of matter, means, methods, or steps, presently existing or later to be developed that perform substantially the same function or achieve substantially the same result as the corresponding embodiments described herein may be utilized according to the invention. Accordingly, the appended claims are intended to include within their scope such processes, machines, manufacture, compositions of matter, means, methods, or steps.

The invention claimed is:

1. A medical scope system comprising:
a medical scope including a scope shaft, a handle attached to the scope shaft having a plurality of control buttons disposed along at least one surface of the handle, two or more of the control buttons including a depression activation circuit operable to create a depression activation signal when pressed, and a touch detection circuit operable to create a touch detection signal when touched, independently of being pressed;
a camera control module including an electronic controller communicatively coupled to the medical scope and operable to receive the depression activation signals and the touch detection signals from the two or more control buttons;
a display device communicatively coupled to the camera control module; and
wherein the camera control module electronic controller is programmed to, in response to receiving a touch detection signal from a respective button of the two or more control buttons, display a function indication on the display device indicating that the respective button is presently being touched and identifying a function that the respective button is configured to activate when the button is pressed in a present mode of operation.

2. The medical scope system of claim 1 wherein the camera control module electronic controller is programmed to display a touch indication communicating that the touched button is presently being touched and identifying the touched button.

3. The medical scope system of claim 1 wherein the camera control module electronic controller is programmed to detect that the touched button is pressed through the depression activation signal, and in response activate the function that the touched button is configured to activate in a present mode of operation.

4. The medical scope system of claim 1, wherein the camera control module is operable to reconfigure the scope into at least two modes of operation in which at least one button function differs between the at least two modes.

5. The medical scope system of claim 1, in which displaying the function indication further includes displaying a list of two or more functions and displaying the touch indication includes highlighting or otherwise visually emphasizing on the display the function associated with the respective touched button.

6. The medical scope system of claim 5, in which displaying the list of two or more functions includes displaying the functions presented in the order of the physical order on the scope device of their associated two or more buttons.

7. The medical scope system of claim 1, in which the camera control module electronic controller is further programmed to, in response to receiving a touch removal signal or in response to a discontinuation of the touch detection signal, remove the displayed function notification.

8. The medical scope system of claim 7, wherein:
the medical scope is further operable to detect a second operator touch of a different, second button on the medical scope and, in response to detecting the second operator touch, transmit a second touch detection signal to a camera control module identifying a second touched button; and
the camera control module electronic controller is further programmed to receive the second touch detection signal at the camera control module and in response, cause the electronic display to display a second function notification indicating that the second touched button is presently being touched and identifying a different, second function that the second touched button is presently configured to activate if pressed or mechanically displaced.

9. A method of operating a medical scope system, the method comprising:
detecting an operator touch of a button on a medical scope, the button capable of both touch detection and pressure or mechanical displacement activation;
in response to detecting the operator touch, transmitting a touch detection signal to a camera control module identifying a touched button among a group of multiple buttons; and
receiving the touch detection signal at the camera control module and in response, causing an electronic display to display a function indication identifying a function that the touched button is presently configured to activate if the button is pressed or mechanically displaced.

10. The method of claim 9 further comprising displaying a touch indication communicating that the touched button is presently being touched and identifying the touched button.

11. The method of claim 10, in which displaying the function indication further includes displaying a list of two or more functions and displaying the touch indication includes highlighting or otherwise visually emphasizing on the display the function associated with the touched button.

12. The method of claim 11, in which displaying the list of two or more functions includes displaying the functions presented in the order of the physical order on the scope device of their associated two or more buttons.

13. The method of claim 9 further comprising detecting that the touched button is pressed, and in response activating the function that the touched button is configured to activate in a present mode of operation.

14. The method of claim 9, further comprising receiving a medical scope mode change control input, and in response changing the function of at least one of the group of buttons will activate if pressed or mechanically displaced.

15. The method of claim 9, further comprising detecting a simultaneous operator touch of two or more buttons in the group of multiple buttons, and in response causing the electronic display to display a multiple function indications communicating that the two or more buttons are touched simultaneously and communicating the functions of each touched button or a different function to be activated if both button are pressed simultaneously.

16. The method of claim 9, further comprising detecting a touch removal from the touched button and, in response, removing the function indication.

17. The method of claim 16, further comprising:
after removing the function indication, detecting a second operator touch of a different, second button on the medical scope and, in response to detecting the second operator touch, transmitting a second touch detection signal to a camera control module identifying a second touched button among the group of multiple buttons; and
receiving the second touch detection signal at the camera control module and in response, causing an electronic display to display a function indication identifying a different, second function that the second touched button is presently configured to activate if pressed or mechanically displaced.

* * * * *